US012678235B2

(12) United States Patent
Roser et al.

(10) Patent No.: US 12,678,235 B2
(45) Date of Patent: Jul. 14, 2026

(54) COMPUTER-IMPLEMENTED METHOD, PROCESSING APPARATUS, IMAGING FACILITY AND COMPUTER PROGRAM FOR SPECIFYING A LOCATION AND/OR A THICKNESS OF A SLICE OF A PATIENT TO BE IMAGED

(71) Applicant: Siemens Healthineers AG, Forchheim (DE)

(72) Inventors: Philipp Roser, Erlangen (DE); Marcus Pfister, Bubenreuth (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/891,451

(22) Filed: Sep. 20, 2024

(65) Prior Publication Data

US 2025/0099186 A1     Mar. 27, 2025

(30) Foreign Application Priority Data

Sep. 21, 2023     (DE) ...................... 10 2023 209 240.9

(51) Int. Cl.
*A61B 34/20*          (2016.01)
*A61B 6/00*           (2006.01)
(Continued)

(52) U.S. Cl.
CPC .............. *A61B 34/20* (2016.02); *A61B 6/025* (2013.01); *A61B 6/12* (2013.01); *A61B 6/54* (2013.01);
(Continued)

(58) Field of Classification Search
CPC ........... A61B 34/20; A61B 6/025; A61B 6/12; A61B 6/54; A61B 6/4441;
(Continued)

(56) References Cited

U.S. PATENT DOCUMENTS

| | | |
|---|---|---|
| 2008/0198966 A1 | 8/2008 | Hjarn |
| 2016/0089090 A1 | 3/2016 | Nakayama |
| 2017/0357772 A1 | 12/2017 | Fischer |

FOREIGN PATENT DOCUMENTS

| | | |
|---|---|---|
| DE | 102016210093 A1 | 12/2017 |
| DE | 102023206678 B3 | 8/2024 |

OTHER PUBLICATIONS

Kroes, Maarten W., et al. "Laser guidance in C-arm cone-beam CT-guided radiofrequency ablation of osteoid osteoma reduces fluoroscopy time." Cardiovascular and Interventional Radiology vol. 40; 2017; pp. 728-734.
(Continued)

*Primary Examiner* — Joel Lamprecht
(74) *Attorney, Agent, or Firm* — Lempia Summerfield Katz LLC

(57)          ABSTRACT

A computer-implemented method for predetermining a location and/or a thickness of a slice, to be imaged of a patient during a tomosynthesis imaging to be parameterized by an imaging facility comprising the steps of obtaining three-dimensional image data of a preceding tomosynthesis imaging or of another three-dimensional imaging of the patient, wherein the three-dimensional image data depicts at least one part of an object located at least partly within the patient, evaluating the three-dimensional image data for establishing the location of a longitudinal axis of the object along which the part of the object extends, and establishing the location and/or the thickness of the slice to be imaged as a function of the established location of the longitudinal axis in such a way that the slice to be imaged images a predetermined target position within the patient and at least one longitudinal section of the object when the longitudinal axis of the object is located in the established location.

15 Claims, 2 Drawing Sheets

(51) Int. Cl.
A61B 6/02 (2006.01)
A61B 6/12 (2006.01)
(52) U.S. Cl.
CPC ..... *A61B 6/4441* (2013.01); *A61B 2034/2065* (2016.02)
(58) Field of Classification Search
CPC ............ A61B 2034/2065; A61B 6/488; G16H 30/20; G16H 30/40
See application file for complete search history.

(56) References Cited

OTHER PUBLICATIONS

RadiAnt DICOM Viewer; "3D Multiplanar reconstruction (MPR)", User Manual version 2021.2; https://www.radiantviewer.com/dicom-viewer-manual/3d-multiplanar-reconstructions.html; 2021; p. 171.
WaybackMachine: "Percutaneous Lung Biopsy", London Health Sciences Centre; in: https://web.archive.org/web/20220927220513/https://www.lhsc.on.ca/thoracic-surgery/percutaneous-lung-biopsy; Sep. 27, 2022; pp. 1-3.

FIG 3

COMPUTER-IMPLEMENTED METHOD, PROCESSING APPARATUS, IMAGING FACILITY AND COMPUTER PROGRAM FOR SPECIFYING A LOCATION AND/OR A THICKNESS OF A SLICE OF A PATIENT TO BE IMAGED

CROSS REFERENCE TO RELATED APPLICATIONS

This application claims the benefit of DE 10 2023 209 240.9 filed on Sep. 21, 2023, which is hereby incorporated by reference in its entirety.

FIELD

Embodiments relate to a computer-implemented method for specifying a location and/or a thickness of a slice of a patient to be imaged.

BACKGROUND

An interventional imaging enables the automatic or manual guidance of an elongated, essentially stiff object, for example a biopsy needle, to specific positions within a patient, for example to the position of a suspected tumor, to be monitored and/or supported. An optimal detection of the positions and orientation of the object would be possible per se on the basis of a three-dimensional imaging of the entire potentially relevant region of the patient. A computed tomography with a high imaging rate may for example be carried out for this. The use of computed tomography for real-time imaging may however greatly restrict access to the patient and is moreover typically linked to a relatively high radiation load for the patient.

Therefore, a fluoroscopy, in which there is continuous or quasi continuous two-dimensional imaging with a relatively low x-ray dose, is frequently used for monitoring or controlling guidance of an object. Here however it is necessary as a rule, within the framework of the guidance of the object, to switch multiple times between two recording geometries offset by 90°, wherein on the one hand a fluoroscopy takes place of which the direction of projection runs approximately parallel to the longitudinal axis of the object, and on the other hand a fluoroscopy of which the directions of projection are approximately at right angles on the longitudinal axis. The required pivoting of the recording geometry and thus of a C-arm for example by 90° during the guidance of the object may however significantly disrupt the workflow.

BRIEF DESCRIPTION AND SUMMARY

The scope of the present disclosure is defined solely by the claims and is not affected to any degree by the statements within this summary. The present embodiments may obviate one or more of the drawbacks or limitations in the related art. Independent of the grammatical term usage, individuals with male, female or other gender identities are included within the term.

Embodiments specify an improved approach for detecting a relative location of an object with regard to a target position and for example to support the guidance of the object to the target position.

Embodiments provide a computer-implemented method for specifying a location and/or a thickness of a slice of a patient to be imaged with a tomosynthesis imaging to be parameterized by an imaging facility, that includes the following steps: obtaining three-dimensional image data of a preceding tomosynthesis imaging or another three-dimensional imaging of the patient, wherein the three-dimensional image data depicts at least a part of an object located at least in part inside the patient, evaluating the three-dimensional image data to establish the location of a longitudinal axis of the object along which the part of the object extends, and establishing the location and/or the thickness of the slice to be imaged as a function of the location of the longitudinal axis established in such a way that the slice to be imaged on the one hand on the one hand images a predetermined target position within the patient and on the other hand images at least one longitudinal section of the object when the longitudinal axis of the object is located in the position established.

Provided both a sufficient longitudinal section of the object and also the target position, thus for example the region of a tumor to be biopsied, is imaged by the tomosynthesis the movement of the object for guidance to the target position may be visualized and/or controlled just as well as when computed tomography is used. Compared to using normal computed tomography however the access to the patient is less greatly restricted and the x-ray dose radiated in with the same image rate is typically significantly lower.

Since with a tomosynthesis imaging however only relatively thin slices may be imaged, a usual tomosynthesis imaging, in which a fixed predetermined location and thickness of the slice to be imaged is used, is not suitable however in many application cases for guiding an object to the target position in a robust manner, since even small deviations from a planned movement path of the object may lead to the end of the object facing towards the target position leaving the slice to be imaged. Such deviations may occur for example with a guidance of the object or due to tolerances of an automated guidance of the object and/or with a diversion of the object from an intended path due to tissue properties of the patient or the like.

This problem may be avoided by the explained adaptation of the slice to be imaged by the following tomosynthesis imaging depending on the location of the longitudinal axis so that, through the procedure explained, a robust guidance to the target of the object with a fluid workflow, good accessibility to the patient and a low radiation load on the patient may be combined.

The longitudinal section of the object is for example a section that extends in the direction of the longitudinal axis. The direction in which the longitudinal axis extends, in the coordinate system of the object, is for example that direction in which the object or at least its imaged part has the maximum extent.

The preceding tomosynthesis imaging or the other three-dimensional imaging and/or the tomosynthesis imaging to be parameterized may be undertaken outside of the claimed method. For example, the claimed method may be carried out entirely within a time interval between the conclusion of the preceding tomosynthesis imaging or the other three-dimensional imaging and the beginning of the tomosynthesis imaging to be parameterized.

As an alternative the method may however also include carrying out the preceding tomosynthesis imaging and or the tomosynthesis imaging to be parameterized or the other three-dimensional imaging. For example, it may be carried out as a part of an interventional imaging in order to adjust the slice to be imaged as a function of the location of the longitudinal axis established, so that the longitudinal section of the object may be robustly imaged. What may be achieved for example by this is that the end of the object facing towards the target position does not leave the slice to be imaged.

The tomosynthesis imaging to be parameterized and the preceding tomosynthesis imaging may use the same imaging facility and are for example carried out directly after one another or a short time after one another, for example after a period of less than 5 minutes or of less than 1 minute or of less than 30 seconds.

If the tomosynthesis imaging to be parameterized and the preceding tomosynthesis imaging or the other three-dimensional imaging are carried out by different imaging facilities, then their coordinate systems may first of all be registered with one another in the usual way.

The respective tomosynthesis imaging for example includes the acquisition of a number of x-rays of the patient from different angles by the imaging facility and the reconstruction of three-dimensional image data of an imaged slice from the x-rays. The other three-dimensional imaging may include a computed tomography or a magnetic resonance tomography or a positron emission tomography or an ultrasound imaging for example.

The slice to be imaged is for example spanned by a length and a width and the thickness of the slice to be imaged. The length, width and thickness may each correspond to dimensions of the slice to be imaged in spatial directions that are at right angles to one another, namely the length direction, the width direction, and the thickness direction of the slice to be imaged. The plane spanned by the length and width or the length direction and the width direction of the slice to be imaged may also be considered as the image plane, that for example is at right angles to the direction of projection of the imaging for an average imaging angle of an angular range to be covered within the framework of the tomosynthesis to be parameterized.

For example, an orientation of the slice to be imaged or of the image plane or of the normals of the image plane and/or a position of the slice to be imaged may be determined as the location of the slice to be imaged.

The location of the slice to be imaged may be selected in such a way that the longitudinal axis of the object is parallel to an image plane spanned by a length and a width of the slice to be imaged or is inclined at an angle of less than 45° or less than 30° or less than 15° to the image plane. For example, the longitudinal axis of the object may lie in the image plane or intersect with the plane, for example within the slice to be imaged. The image plane may for example be arranged centrally within the slice to be imaged in the direction of the thickness of the slice to be imaged.

As a rule, for example when the object involved is a needle, for example a biopsy needle, it may be assumed that the object is moving between consecutive imagings approximately in parallel to the longitudinal axis of the object. If the slice to be imaged is selected in such a way that the image plane runs at least roughly approximately in parallel to the longitudinal axis, a movement of the object thus only leads to a relatively small shift of the object at right angles to the image plane or in the thickness direction of the slice to be imaged.

Since the thickness of the slice to be imaged in the tomosynthesis imaging is typically significantly smaller than the extent of the slice at right angles to the thickness direction or within the image plane, this enables the probability to be minimized of relevant parts of the object, for example the tip of a biopsy needle, lying outside the slice in the tomosynthesis imaging to be parameterized and thereby not being imaged.

For example, the location of the slice to be imaged may be selected so that both the longitudinal axis of the object and also the target position lie within the image plane. This makes possible an optimal imaging of the relative position and orientation of the object in relation to the target position itself for a very small thickness of the slice to be imaged or even when, as will be explained later, temporarily only a two-dimensional imaging is carried out.

The use of a small thickness of the slice to be imaged is typically advantageous since in this case, within the framework of the imaging by the imaging facility, only a narrower angular range has to be covered than for a greater thickness of the slice to be imaged. With decreasing thickness of the slice to be imaged this enables higher imaging rates to be achieved or a given imaging rate may be achieved with lower accelerations of components of the imaging facility.

The thickness of the slice to be imaged may be selected in such a way that the target position and/or an end of the object in the direction of the longitudinal axis, of which the position is established as a function of the three-dimensional image data, each have at least a predetermined minimum distance from boundary surfaces of the slice to be imaged in the direction of the thickness.

The predetermination of the minimum distance enables it to be ensured that, with a certain movement of the patient and/or of the object in relation to the imaging facility and thus in relation to the slice to be imaged, the target position or the end of the object lie within the slice to be imaged during the tomosynthesis imaging to be parameterized, whereby the position and orientation of the object in relation to the target position may be well visualized or evaluated on the basis of the parametrized tomosynthesis imaging.

To determine the location of the slice to be imaged at least one of the following variables or a weighted sum that includes a number of or all of the following variables as summands may be minimized: an angle between the longitudinal axis of the object in the location of the longitudinal axis established and the or an image plane spanned by a length and width of the slice to be imaged, a distance between the target position and the middle of the slice to be imaged in the direction of the thickness of the slice to be imaged, and/or a distance between the or an end of the object in the direction of the longitudinal axis of the object, the position of which is established as a function of the three-dimensional image data, from the middle of the slice to be imaged in the direction of the thickness of the slice to be imaged.

This optimization of the location of the slice to be imaged allows the selection of a relatively small thickness of the slice to be imaged, without risking relevant features in the tomosynthesis imaging to be parameterized lying outside the slice to be imaged.

To predetermine an orientation of the slice to be imaged, an average imaging angle of a range of angles to be covered by the imaging facility within the framework of the tomosynthesis imaging to be parameterized may be predetermined.

The minimization of the at least one variable or of the weighted sum for determining the location of the slice to be imaged may be undertaken under boundary conditions that the average recording angle is restricted to a predetermined angular interval. For example, such a restriction may be necessary due to a restricted mobility of the imaging facility, for example of a C-arm, or it may be expedient in order not to disturb or restrict medical personnel or at least to do so as little as possible.

To predetermine the location of the slice to be imaged the orientation and/or the position of the slice to be imaged may be predetermined. The position of the slice to be imaged may be predetermined for example by selecting the isocenter of the tomosynthesis imaging to be parameterized. The position may be predetermined in such a way that the distances between relevant features, i.e. for example the target position and the end of the object, from edges of the slice to be imaged in the thickness direction and/or the length direction and/or the width direction of the slice to be imaged and/or a weighted sum, that includes these distances as summands, are maximized.

A two-dimensional x-ray imaging may be carried out before the tomosynthesis imaging to be parameterized, always or when an imaging condition is fulfilled, wherein an imaging geometry of the two-dimensional x-ray imaging is predetermined as a function of the location of the longitudinal axis of the object established. The two-dimensional imaging may be carried out once or a number of times or continuously, for example as fluoroscopy, before the tomosynthesis imaging to be parameterized.

A C-arm, that carries the x-ray source, and the x-ray detector may be controlled for predetermining the imaging geometry for example. The two-dimensional imaging may for example be carried out in such a way that the projection plane of the two-dimensional imaging is parallel to the image plane of the tomosynthesis imaging to be parametrized and/or that the projection direction of the two-dimensional imaging is at right angles to this image plane.

For example a two-dimensional imaging may first be carried out after a respective tomosynthesis imaging, at least when, with the aid of this, a suitable imaging geometry may be selected and thus the imaging condition is fulfilled, for a predetermined time interval or until a trigger condition is fulfilled, in order for example to allow higher imaging rates and/or to reduce a radiation load on the patient. For example the tomosynthesis imaging to be parameterized may then be carried out at regular intervals or on fulfillment of the trigger condition in order to acquire three-dimensional image data, on the basis of which the location of the object or of its longitudinal axis may be determined once again in order to adjust the imaging.

In the method a provisional target position in a reference coordinate system of a three-dimensional reference image dataset may be predetermined, wherein the reference image dataset images the patient at least partly. The reference coordinate system of the three-dimensional reference image dataset is registered with a facility coordinate system defined in relation to the imaging facility, in order to transfer the provisional target position into the facility coordinate system and thus to predetermine the target position.

The registration of the reference coordinate system with the facility coordinate system may be undertaken on the basis of the reference image dataset and at least two two-dimensional x-rays of the patient by the imaging facility, that are recorded with imaging angles that differ from one another by at least 30° or at least 60°. For example, the imaging angles or projection directions of the two-dimensional x-ray image may be at least approximately at right angles to one another. For one of the x-rays, for example the projection direction may run at least approximately parallel to the longitudinal axis of the object and for the other of the x-rays may be at least approximately at right angles to the longitudinal axis.

The reference image dataset may for example involve a computed tomography or a magnetic resonance tomography of the patient. The reference image dataset may for example serve to recognize and predetermine a target position to which the object is to be guided, automatically or also manually, within the framework of the image data evaluation and to mark it in the reference image dataset in order to predetermine the provisional target position.

The reference image dataset may for example be acquired by another imaging facility than that used for tomosynthesis imaging. The reference image dataset may for example be acquired well before the tomosynthesis imaging in time, for example one or more days before.

For example for capturing the x-rays used for registration, the two recording geometries may be used, between which in the prior art, as was explained at the outset, within the framework of the supervision of a biopsy or of similar processes, repeated switches are made by a fluoroscopy. By contrast with the procedures described there, the marked change in the recording geometry associated therewith, for example the pivoting of a C-arm by 90°, is only required once however for registration and does not have to be carried out within the framework of the supervision.

To predetermine the thickness of the slice to be imaged, for example the width of the angular range to be covered by the imaging angle within the framework of the tomosynthesis imaging to be parameterized is predetermined. In addition or as an alternative, to predetermine the position of the slice to be imaged, the position of an isocenter of the tomosynthesis imaging to be parameterized is predetermined.

The projection direction for the average imaging angle of the angular range for example corresponds to the thickness direction of the slice to be imaged. The slice thickness able to be imaged for a given imaging quality is predetermined by the angular range covered. The isocenter of the tomosynthesis imaging to be parameterized may be shifted in order to shift the region imaged. A tilting of the imaged region or the predetermining of the orientation of the slice to be imaged may be undertaken as explained above.

In the method a respective tomosynthesis imaging may be carried out repeatedly. The three-dimensional image data of the last tomosynthesis imaging carried out in each case may be used in order to parameterize the respective following tomosynthesis imaging as the tomosynthesis imaging to be parameterized in each case in order to predetermine the location and/or the thickness of the respective slice of the patient to be imaged. Through this, as has already been explained above, an adjustment of the imaging may be achieved.

The location of the longitudinal axis of the object and/or of further image data that is acquired within the framework of the tomosynthesis imaging to be parameterized may be evaluated in order to provide at least one control parameter for activation of an actuator system for automatic movement of the object to the target position and/or visualization for a user via a display facility in order to support the user during guidance of the object to the target position.

After the establishment of the location and/or the thickness of the slice to be imaged an imaging facility and/or components of the imaging facility may be activated, so that three-dimensional image data describing the slice to be imaged by the imaging facility within the framework of a tomosynthesis imaging parameterized by the location and/or the thickness may be acquired. This is also possible when the acquisition of the three-dimensional image data of the patient by the preceding tomosynthesis imaging is undertaken outside the method or when this three-dimensional image data is acquired by three-dimensional imaging that differs from the three-dimensional tomosynthesis imaging.

In the method the imaging of a cuboid slice with constant thickness may be parametrized.

It is however also possible for the slice to be imaged to be a wedge-shaped slice. This may be expedient since, for example in a biopsy even slight deviations of the insertion geometry may lead to marked deviations of the position of the tip of the biopsy needle for deeper insertions. This may be compensated for, for example, by a wedge-shaped slice being imaged, that becomes thicker as the distance from the insertion point increases. A suitable choice of the recording geometries used within the framework of the tomosynthesis imaging enables the same maximum slice thickness to be achieved with a wedge-shaped slice potentially with a smaller angular range to be covered by the imaging angle as would be the case for a cuboid-shaped slice. Thus by imaging a wedge-shaped slice potentially the required movement of components used for imaging, for example of a C-arm, is reduced.

The location of the wedge-shaped slice to be imaged is established in such a way that the thickness of the slice to be imaged varies in a direction of variation that runs in parallel to the longitudinal axis of the object or is inclined at an angle of less than 45° or less than 30° or less than 15° to the longitudinal axis. In addition or as an alternative the location of the wedge-shaped slice may be established in such a way that its thicker end is facing away from the insertion point of a biopsy needle or other needle used as an object.

If a wedge-shaped slice is imaged, the maximum slice thickness, the minimum slice thickness and/or an average slice thickness may be determined as the established thickness of the slice to be imaged for example. If only one of the thicknesses is predetermined by the method explained above, one of the other thicknesses for example may be permanently predetermined or predetermined via a fixed relationship with the slice thickness established.

As well as the computer-implemented method, embodiments relate to a processing apparatus that is configured to carry out the computer-implemented method.

Embodiments further provide an imaging facility that is configured to acquire three-dimensional image data of a slice to be imaged of a patient by a tomosynthesis imaging, wherein the imaging facility is configured to carry out the computer-implemented method. The imaging facility may for example be an x-ray facility. The imaging may in this case be undertaken by at least one x-ray source and by at least one x-ray detector, for example by emission of x-rays by the x-ray source for fluoroscopy of the patient and detection of the x-rays by the x-ray detector after their interaction with the patient. For example an examination volume of the imaging facility may be accessible during the imaging. This may be achieved for example by use of a C-arm or O-arm x-ray facility as the imaging facility.

For example the imaging facility or a control facility of the imaging facility may be configured, as explained above, to activate individual components of the imaging facility, for example an x-ray source, an x-ray detector and/or an actuator system for moving these components or for example a C-arm that bears these components in order to carry out the tomosynthesis imaging parameterized by the thickness and/or location of the slice to be imaged.

Embodiments provide a computer program, including program instructions that are embodied to carry out the computer-implemented method when they are executed on a data processing facility.

Embodiments provide a data medium that includes the computer program.

Further advantages and details emerge from the embodiments given below, as well as from the associated figures. In the figures, in schematic diagrams:

BRIEF DESCRIPTION OF THE FIGURES

FIG. 3 depicts a flow diagram of the method used in FIG. 1 for parametrization of the slice according to an embodiment.

DETAILED DESCRIPTION

Figure 1:
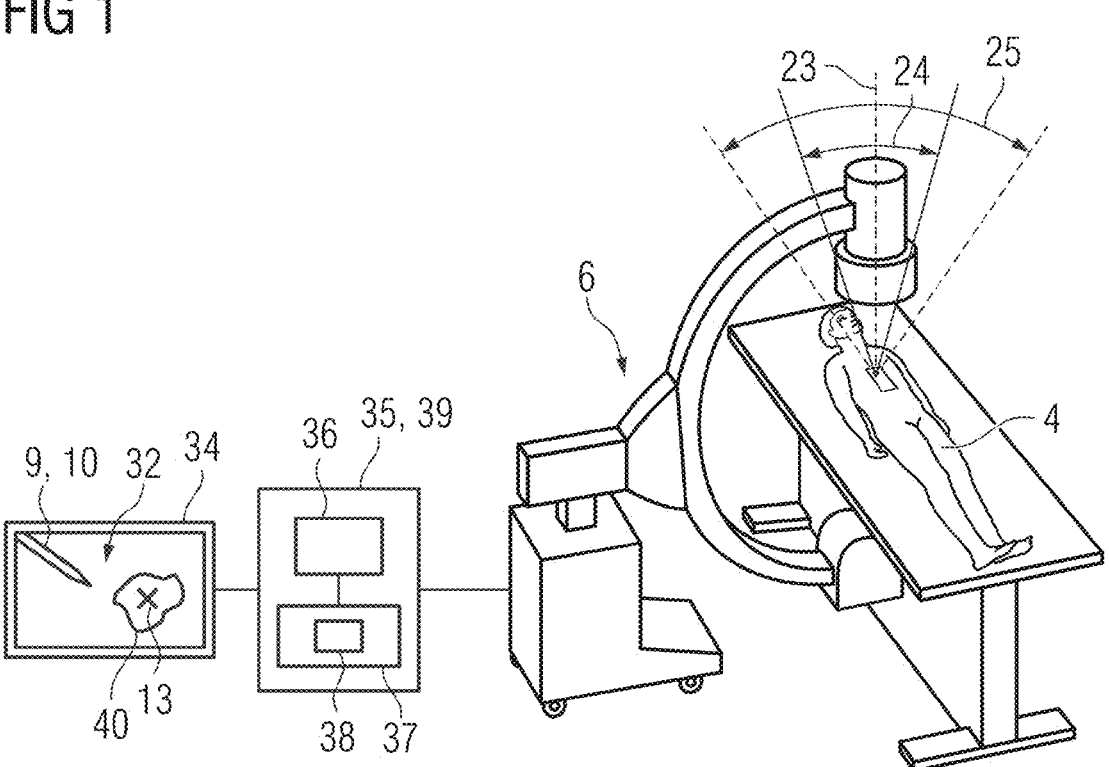
FIG. 1 depicts an embodiment of a processing apparatus that is configured to implement an embodiment of the computer-implemented method for predetermining a location and a thickness of a slice to be imaged in a tomosynthesis imaging.

FIG. 1 depicts a schematic of tomosynthesis imaging on a patient 4 by an imaging facility 6. Here, in the way known per se, a number of x-rays of the patient 4 are acquired from various imaging angles with an angular range 24 covered within the framework of the imaging and a processing apparatus 39 reconstructs three-dimensional image data from this. Then, on the basis of the three-dimensional image data, there may be a visualization 32 of relevant features on a display facility 34, for example by individual slices or a generated artificial projection image being output.

In the example the imaging is intended to support a user, not shown in the figure, in a guiding an object 10, for example a biopsy needle, within the patient 4 to a target position 13, for example to a potential tumor 40. As an alternative it would also be possible for example, on the basis of the three-dimensional image data, to activate an actuation system not shown in the figure in order to guide the object 10 automatically to the target position 13.

What is problematic here however is that the angular range 24 covered typically is to be kept as small as possible in order to avoid disturbing medical personnel in the area of the patient 4 and in order to make high imaging rates possible. With tomosynthesis imaging however this leads to only relatively thin slices being able to be imaged with sufficient quality. Therefore, with a fixed predetermination of the slice to be imaged, as is used in usual tomosynthesis imagings, even a relatively small movement of the patient 4 or of the object 10 in relation to the imaging facility 6 lead to features relevant for the guidance of the object 10 lying outside the imaged slice and thus not being able to be imaged.

Therefore a method is implemented by the processing apparatus 39 for predetermining the location and the thickness of the slice to be imaged of a tomosynthesis imaging parameterized on the basis of three-dimensional image data of a preceding tomosynthesis imaging, that will be explained below with additional reference to FIGS. 2 and 3. This method makes it possible for example to adjust the parametrization of the slice in such a way that a relevant longitudinal section 14 of the object 10 and the target position 13 may typically be imaged in a robust manner. It may also be sufficient exclusively to adjust the location or the thickness of the slice to be imaged dynamically, wherein an adaptation of the two variables is typically advantageous.

Figure 2:
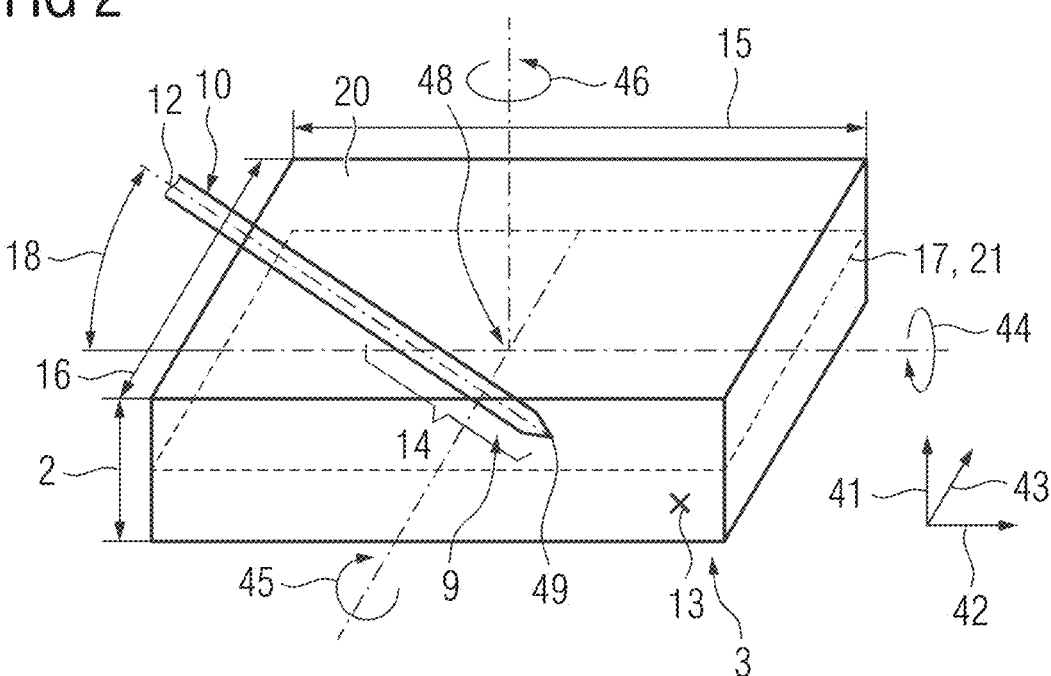
FIG. 2 depicts a schematic diagram of a slice to be parameterized by the method used in FIG. 1 according to an embodiment.
Figure 3:
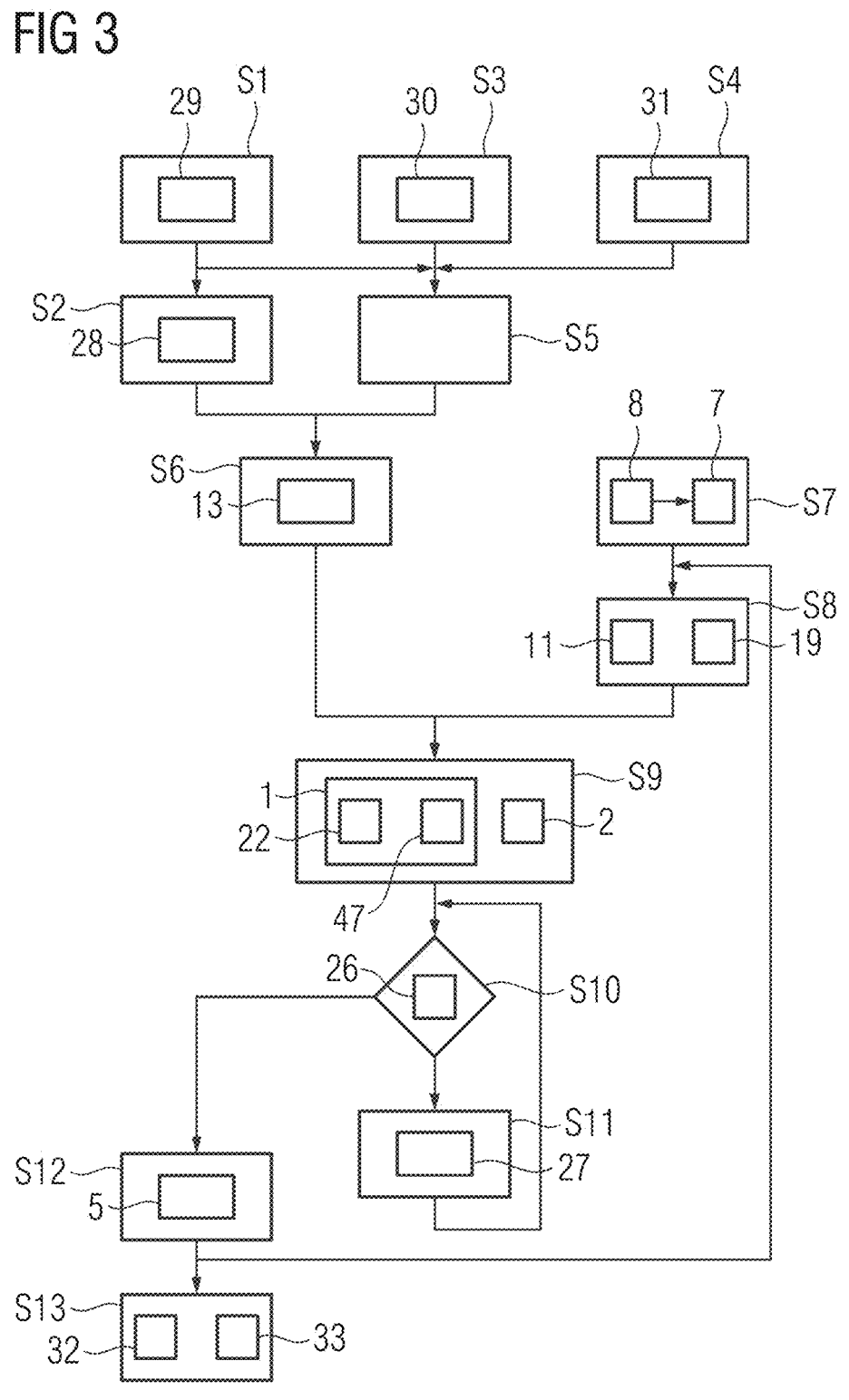

FIG. 2 depicts a schematic diagram of a slice 3 to be parameterized and of features that are taken into account in the parametrization of the slice 3, while FIG. 3 depicts a flow diagram of the method used.

The actual flow diagram shown in FIG. 3 represents an especially advantageous embodiment of the method and also includes preparatory or subsequent steps that do not necessarily have to be part of the method. Therefore, for better understanding, first of all the central method steps will be briefly explained before the overall method is described in detail.

The parameterization of the tomosynthesis imaging to be parameterized 5, or in concrete terms the predetermination of the location 1 and the thickness 2 of the slice to be imaged 3, is based on three-dimensional image data 7 of a preceding tomosynthesis imaging 8 of the patient 4, that images at least one part 9 of the object 10 located at least partly within the patient 4.

Since in the example a tomosynthesis imaging 5, 8 undertaken at relatively short intervals during ongoing operation is to be parameterized, the three-dimensional image data 7 in the example involves image data 7 acquired in step S7 by the imaging facility 6. In principle the image data 7 in step S7 could however also originate from another source, i.e. be read out for example from a database that stores image data 7 of a tomosynthesis imaging 8 concluded before the beginning of the method.

Subsequently, in step S8, the three-dimensional image data 7 is evaluated by the processing apparatus 39 in order to establish at least the location 11 of the longitudinal axis 12 of the object 10. Then, in step S9, the location 1 and the thickness 2 of the slice to be imaged 3 is predetermined, as will be explained further on in detail, as a function of the location 11 of longitudinal axis 12 established, in such a way that the slice to be imaged 3 on the one hand depicts the predetermined target position 13 within the patient 4 and on the other hand depicts the longitudinal section 14 of the object 10 when the longitudinal axis 12 of the object 10 is located in the established location 11.

To put it differently, the slice 3 is for example parameterized so that, at least for the current object position, all relevant features for guidance of the object 10 to the target position 13 may be depicted. For example when the parameterization of the slice 3 takes account of a likely direction of movement of the object 10, that for example for needles, catheters and the like typically coincides with the longitudinal axis, what may be achieved is that even with relatively large movements of the object 10 between the tomosynthesis imagings 5, 8, the relevant features may also be robustly imaged in the tomosynthesis imaging to be parameterized 5 subsequently carried out. Thus the method for predetermining the location 1 and thickness 2 of the slice to be imaged 3 could for example already be implemented by steps S7 to S9.

The design of the method shown in FIG. 3 is explained in detail below wherein, for better understanding, the slice 3 parameterized in FIG. 2 is additionally still included in the diagram.

First of all, in step S1, a three-dimensional reference image dataset 29 is acquired, that images the patient 4 at least partly. The reference image dataset 29 may for example be a dataset acquired by computed tomography, magnetic resonance tomography or positron emission tomography, ultrasound imaging or similar methods.

In step S2 a provisional target position 28 to which the object 10 is to be guided at a later point in time is defined in the reference image dataset 29. For example, a potential tumor 40 that is to be biopsied may be identified automatically or by medical personnel.

The reference image dataset 29 is typically acquired by an imaging facility other than the imaging facility 6 used for the tomosynthesis imaging 5,8 or at least the patient 4 is frequently not located during the acquisition of the reference image dataset in the exact same location in relation to the imaging facility 6 as was the case during the acquisition of the reference image dataset 29. Therefore the reference coordinate system of the three-dimensional reference image dataset 29 should first of all be registered with the facility coordinate system of the imaging facility 6.

For this purpose, after the positioning of the patient 4 in the imaging facility 6, first of all, in the steps S3 and S4, a two-dimensional x-ray image 30, 31 is recorded. Markedly different imaging angles are used here for recording the x-ray images 30 and 31.

For example, the x-ray images 30 may be acquired with an imaging geometry in which the projection direction essentially runs parallel to the location of the longitudinal axis 12 of the object 10 assumed or planned before the intervention. Then, for the x-ray image 31 a projection direction may be used that is essentially at right angles to the projection direction for the x-ray image 30.

The use of markedly different imaging geometries may for example require a pivoting of a C-arm by 90°, that may have a disruptive effect for medical personnel in the area of the patient 4. By contrast with the repeated switching between corresponding imaging geometries mentioned at the start that is typically required with a fluorescence imaging for monitoring of the guidance of the object 10 to the target position 13, this type of major change in the imaging geometries in the method explained is only required once however for preparation of the intervention.

Then, in step S5, on the basis of the reference image dataset 28 and the two-dimensional x-rays 30, 31, a registration of the reference coordinate system with the facility coordinate system may be carried out. Approaches to registration of three-dimensional image data with two-dimensional image data recorded from a number of perspectives are known per se and will therefore not be explained in greater detail.

In step S6, since the coordinate systems are now registered with one another, the target position 13 in the facility coordinate system is now determined from the provisional target position 28 in the reference coordinate system.

Then, in step S7, a first tomosynthesis imaging 8 may take place in order to provide the three-dimensional image data 7 of the slice imaged by this tomosynthesis imaging 8.

The initial choice of the location 1 and thickness 2 of the slice to be imaged 3 may be made here for example on the basis of intervention planning, that may be carried out for example with the aid of the reference image dataset 29 and thus, due to the preceding registration of the coordinate systems in step S5, may be transferred to the facility coordinate system. For example in the reference image dataset, as well as the target position, an insertion point for the object 10 may be predetermined and within the framework of the parameterization of the tomosynthesis imaging it may first be assumed that the longitudinal axis 12 of the object 10 runs at least approximately parallel to the straight lines connecting insertion point and target position 13.

In step S8 the three-dimensional image data 7 of the preceding tomosynthesis imaging 8 is evaluated, in order on the one hand to establish the location 11 of the longitudinal axis 12 of the object 10 and on the other hand, additionally in the example, to establish the position of the end 49 of the object 10 in the direction of the longitudinal axis 12. Thus, if the object 10 involves a biopsy needle for example, then its alignment and the position of its tip is determined. Artificial objects, for example biopsy needles, as a rule generate sufficient contrast during a tomosynthesis imaging in order for example to make possible a fully automated segmentation of such an object 10, so that the variables may be established without problems.

Subsequently, in step S9, on the basis of the location 11 of the longitudinal axis 12 and additionally in the example the position of the end 13 of the object 10, the location 1 and on the other hand the thickness 2 of the slice to be imaged 3 in the tomosynthesis imaging to be parameterized is established. Here in the example first of all the location 1 of the slice 3 or of an image plane 17 that is spanned by the longitudinal direction 42 and the width direction 43 and lies centrally in relation to the thickness 2 of the slice 3, is optimized. Here, in relation to the location 1, an orientation 22 of the slice 3 or the image plane 17 and the position 47 of the slice 3 may be predetermined.

As is shown schematically in FIG. 2 by the arrows 44 to 46, the slice to be imaged 3 may be turned for predetermining the orientation 22 about a number of axes of rotation, that are each parallel to the thickness direction 41, to the length direction 42 or to the width direction 43. The orientation may be set here by selecting the average recording angle 23 of an angular range 24 to be covered within the framework of the tomosynthesis imaging 5 to be parameterized by the imaging facility 6. Depending on the embodiment of the imaging facility 6 a pivoting of the slice to be imaged 3 about all three axes of rotation may be possible or only parts of this rotation may be possible. The position 47 of the slice 3 may be adapted by the isocenter 48 of the tomosynthesis imaging being shifted.

For determining the location 1 of the slice to be imaged 3 a weighted sum is minimized in the example, that has the following variables as summands: the angle 18 between the longitudinal axis 12 of the object 10 and the image plane 17, the distance between the target position 13 and the middle 21 of the slice to be imaged 3 in the direction of the thickness 2 of the slice to be imaged 3, and the distance between the end 49 of the object 10 and the middle 21 of the slice to be imaged 3 in the direction of the thickness 2.

As has already been shown in detail in the general parts, such a selection of the location of the slice 3 makes possible the use of especially thin slices during the imaging and thus for example of high imaging rates or of small angular ranges covered during the imaging.

As an alternative or in addition, within the framework of the optimization, the distances between relevant features, i.e. for example the target position 13 and the end 49 of the object 10 and the edge surfaces of the slice to be imaged may be maximized in the length direction 42 and/or the width direction 43 of the slice to be imaged, for example by them being included with negative weights in the weighted sum to be minimized.

Due to the embodiment of the imaging facility 6 or in order to ensure that access to the patient 4 for medical personnel is possible without problems during the imaging, it may be expedient to restrict the imaging geometry for the tomosynthesis imaging to be parameterized 5. Therefore, for example the weighted sum is minimized under the boundary condition that the average recording angle 23 is restricted to a predetermined angular interval 25.

As shown schematically in FIG. 2, the location 1 or the orientation 22 of the slice to be imaged 3 may be selected in such a way that the longitudinal axis 12 of the object 10 is inclined at an angle 18 of less than 30° to the image plane 17. In the example in accordance with FIG. 2, to illustrate this more clearly, a relatively large angle 18 is used.

What is achieved within the framework of the optimization explained above is that the angle 18 is still far smaller than in FIG. 2 and the longitudinal axis 12 may for example be at least approximately parallel to the image plane 17. As has already been explained in the general part, it may be made possible by this for the object 10 to be shifted over large distances without it leaving the slice 3 to be imaged. The adjustment of slice 3 is thus less time-critical, whereby longer times may be allowed between the tomosynthesis imaging 5, 8.

The thickness 2 of the slice to be imaged 3 is selected in the example in such a way that the target position 13 and the end 49 of the object 12 each have a predetermined minimum distance from the boundary surfaces 20 of the slice to be imaged 3 in the thickness direction 41 of the slice to be imaged 3. The thickness of the slice to be imaged is predetermined in the example by the width of the angular range 24 to be covered by the recording angle within the framework of the tomosynthesis imaging 5 to be parameterized.

The tomosynthesis imaging 5 to be parameterized may be carried out following on directly from step S9. In the example however, as far as possible, there may first be a two-dimensional x-ray imaging 27 temporarily between the tomosynthesis imagings 5, 8, for example a fluoroscopy, that with the same imaging rates may lead to a lower radiation load on the patient 4.

Therefore, in step S10, a check is first made as to whether an imaging condition 26 is fulfilled, the fulfillment of that implies the reliability of two-dimensional x-ray imaging 27. In the example the imaging condition 26 on the one hand evaluates the angle 18 between the image plane 17 and the longitudinal axis 12 of the object 10 and the distances between the target position 13 and the previously established positions 19 of the end 49 of the object 10 and the boundary surfaces of the slice 3 parameterized beforehand and on the other hand a period of time interval since the preceding tomosynthesis imaging 8. Here the time interval may for example be compared with a limit value that depends on the angle at the distances. To put it another way, the two-dimensional imaging 27 may be allowed for a certain time if it is very unlikely, due to sufficiently large distances and a sufficiently flat angle 18 for sufficiently long periods of time, that relevant features will leave the imaged slice 3.

If the imaging condition 26 is fulfilled in step S17, then in in step S11, first of all a two-dimensional x-ray imaging 27 is undertaken, after which step S10 is repeated, for example in order to check whether the limit value for the time interval from the last tomosynthesis imaging 8 has already been exceeded.

If the imaging condition 26 is not fulfilled or is no longer fulfilled in step S10, then in step S12 there is an activation of the imaging facility 6 for carrying out the tomosynthesis imaging to be parameterized 5. This is used, in step S13, to output a visualization 32 of the slice or relevant image contents via a display facility 34 to the user and/or to output control signals 33 for an actuator system (not shown) for automatic movement of the object 10.

On the basis of the three-dimensional image data of the tomosynthesis imaging 5 carried out in step S12, the method steps are repeated as from step S8, in order for example to adjust the imaged slices 3 iteratively over a number of tomosynthesis imaging.

The method steps explained are implemented in the example by the processing apparatus 39. This is implemented in the example in that programmable data processing facilities 35 with a processor 36 and a memory 37 are programmed by a suitable computer program 38. The processing apparatus 39 may for example be a workstation computer, be integrated into the imaging facility 6, be provided by a server or also be implemented as a Cloud solution.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for determining at least one of a location or a thickness of a subsequent slice of a patient by an imaging facility using tomosynthesis imaging, the method comprising:

obtaining three-dimensional image data of the patient from a previously performed imaging procedure, wherein the imaging procedure comprises tomosynthesis imaging or another three-dimensional imaging of the patient, wherein the three-dimensional image data depicts at least a part of an object located at least partly within the patient;

determining, by at least one processor, a location of a longitudinal axis of the object based on the three-dimensional image data;

determining, by the at least one processor, at least one of the location or the thickness for the subsequent slice based at least in part on the location of the longitudinal axis, wherein at least one of the location or the thickness of the subsequent slice is determined so as to encompass a predetermined target position within the patient and at least one longitudinal section of the object; and generating at least one control parameter, based on at least one of the location or the thickness, the at least one control parameter used for controlling the imaging facility to perform the tomosynthesis imaging of the subsequent slice.

2. The computer-implemented method of claim 1, wherein the location of the subsequent slice is determined so that the longitudinal axis of the object is parallel to an image plane spanned by a length and a width of the slice to be imaged or is inclined at an angle of less than 45° to the image plane.

3. The computer-implemented method of claim 1, wherein the thickness of the subsequent slice is determined so that at least a predetermined minimum distance exists between boundary surfaces of the subsequent slice in a direction of the thickness and the predetermined target position.

4. The computer-implemented method of claim 1, wherein for determining the location of the subsequent slice, at least one of the following variables is minimized:

an angle between the longitudinal axis of the object and an image plane spanned by a length and width of the subsequent slice;

a distance between the predetermined target position and a middle of the subsequent slice in a direction of the thickness of the subsequent slice; and/or a distance between an end of the object in a direction of the longitudinal axis of the object, a position of which is determined as a function of the three-dimensional image data, from a middle of the subsequent slice in the direction of the thickness of the subsequent slice.

5. The computer-implemented method of claim 4, further comprising:

determining an orientation of the subsequent slice based on an average recording angle of an angular range to be covered within a framework of the tomosynthesis imaging.

6. The computer-implemented method of claim 5, wherein the average recording angle is restricted to a predetermined angular interval.

7. The computer-implemented method of claim 1, further comprising wherein a two-dimensional x-ray imaging is carried out prior to the tomosynthesis imaging of the subsequent slice, wherein an imaging geometry of the two-dimensional x-ray imaging is determined as a function of the location of the longitudinal axis of the object.

8. The computer-implemented method of claim 1, further comprising:

determining a provisional target position is in a reference coordinate system of a three-dimensional reference image dataset, wherein the three-dimensional reference image dataset images the patient at least partly, wherein the reference coordinate system of the three-dimensional reference image dataset is registered with a facility coordinate system defined with respect to the imaging facility in order to transfer the provisional target position into the facility coordinate system and to determine a target position.

9. The computer-implemented method of claim 8, wherein the reference coordinate system is registered with the facility coordinate system based on the three-dimensional reference image dataset and further based on at least two two-dimensional x-rays of the patient by the imaging facility that are recorded with recording angles that differ from one another by at least 30°.

10. The computer-implemented method of claim 1, wherein for determining the thickness of the subsequent slice, a width of an angular range to be covered by a recording angle is determined within a framework of the tomosynthesis imaging or that a position of the subsequent slice is determined based on a position of an isocenter of the tomosynthesis imaging.

11. The computer-implemented method of claim 1, wherein a respective tomosynthesis imaging is performed repeatedly, wherein the three-dimensional image data of a prior tomosynthesis imaging procedure carried out is used to control a subsequent tomosynthesis imaging to determine at least one of the location or the thickness of the subsequent slice.

12. The computer-implemented method of claim 1, wherein the location of the longitudinal axis of the object and/or further image data that is acquired using tomosynthesis imaging, is evaluated in order to provide at least one control parameter for activation of an actuator system for automated movement of the object to the predetermined target position or is visualized for a user via a display facility in order to support the user in guidance of the object to the predetermined target position.

13. The computer-implemented method of claim 1, further comprising:

activating an imaging facility using the at least one control parameter.

14. An imaging facility configured to acquire three-dimensional image data of a subsequent slice of a patient by a tomosynthesis imaging, wherein the imaging facility is configured to:

obtain three-dimensional image data from a previously performed tomosynthesis imaging of the patient, wherein the three-dimensional image data of the patient depicts at least one part of an object located at least partly within the patient;

determining, from the three-dimensional image data, a location of a longitudinal axis of the object along which the part of the object extends; and determining at least one of a location or a thickness of the subsequent slice as a function of the location of the longitudinal axis so that the subsequent slice depicts a predetermined target position within the patient and at least one longitudinal section of the object.

15. A non-transitory computer implemented storage medium that stores machine-readable instructions executable by at least one processor for determining at least one of a location or a thickness of a slice to be imaged of a patient for a tomosynthesis imaging by an imaging facility, the machine-readable instructions comprising:

obtaining three-dimensional image data of the patient from a preceding tomosynthesis imaging, wherein the three-dimensional image data of the patient depicts at least one part of an object located at least partly within the patient;

determining a location of a longitudinal axis of the object along which the part of the object extends based on the three-dimensional image data;

determining, at least one of the location or the thickness for the subsequent slice based at least in part on the location of the longitudinal axis, wherein at least one of the location or the thickness of the subsequent slice is determined so as to encompass a predetermined target position within the patient and at least one longitudinal section of the object; and generating at least one control parameter, based on at least one of the location or the thickness, the at least one control parameter used for controlling the imaging facility to perform the tomosynthesis imaging of the subsequent slice.

* * * * *